US008210548B1

(12) United States Patent
Agyemang

(10) Patent No.: US 8,210,548 B1
(45) Date of Patent: Jul. 3, 2012

(54) PORTABLE NURSING SERVICE CART AND ASSOCIATED METHOD

(76) Inventor: June Agyemang, Atlanta, GA (US)

( * ) Notice: Subject to any disclaimer, the term of this patent is extended or adjusted under 35 U.S.C. 154(b) by 502 days.

(21) Appl. No.: 12/541,935

(22) Filed: Aug. 15, 2009

Related U.S. Application Data

(60) Provisional application No. 61/189,254, filed on Aug. 15, 2008.

(51) Int. Cl.
*B62B 3/00* (2006.01)
*A61B 19/02* (2006.01)

(52) U.S. Cl. ..................... 280/47.35; 312/209
(58) Field of Classification Search .......... 280/638–79.7
See application file for complete search history.

(56) References Cited

U.S. PATENT DOCUMENTS

| | | | | |
|---|---|---|---|---|
| 5,314,243 A | * | 5/1994 | McDonald et al. | 312/215 |
| D352,106 S | * | 11/1994 | Fanney et al. | D24/185 |
| 5,536,084 A | * | 7/1996 | Curtis et al. | 700/240 |
| 5,564,803 A | * | 10/1996 | McDonald et al. | 312/215 |
| 5,623,869 A | * | 4/1997 | Moss et al. | 108/43 |
| 5,702,115 A | * | 12/1997 | Pool | 280/47.35 |
| 5,765,842 A | * | 6/1998 | Phaneuf et al. | 280/47.35 |
| 5,806,943 A | * | 9/1998 | Dell et al. | 312/223.3 |
| 6,022,088 A | * | 2/2000 | Metzler | 312/209 |
| 6,339,732 B1 | * | 1/2002 | Phoon et al. | 700/237 |
| 6,374,752 B1 | * | 4/2002 | Walser | 108/50.01 |
| 6,435,109 B1 | * | 8/2002 | Dell et al. | 108/144.11 |
| 6,493,217 B1 | * | 12/2002 | Jenkins, Jr. | 361/679.6 |
| 6,493,220 B1 | * | 12/2002 | Clark et al. | 361/679.41 |
| 6,626,445 B2 | * | 9/2003 | Murphy et al. | 280/47.34 |
| 6,654,378 B1 | * | 11/2003 | Mahany et al. | 370/401 |
| 6,655,545 B1 | * | 12/2003 | Sonneborn | 221/7 |
| 6,715,722 B2 | * | 4/2004 | Roberts | 248/129 |
| 6,722,673 B1 | * | 4/2004 | Hamlin | 280/47.35 |
| 7,009,840 B2 | * | 3/2006 | Clark et al. | 361/679.41 |
| 7,191,950 B1 | * | 3/2007 | Petrovich et al. | 235/472.02 |
| 7,311,254 B2 | * | 12/2007 | Olsen | 235/440 |
| 7,338,055 B2 | * | 3/2008 | Fuentes | 280/79.3 |
| D568,481 S | * | 5/2008 | Martinson | D24/185 |
| 7,367,571 B1 | * | 5/2008 | Nichols | 280/47.18 |
| 7,401,796 B1 | * | 7/2008 | Greco | 280/47.35 |
| 7,461,825 B2 | * | 12/2008 | Olivera et al. | 248/282.1 |
| 7,562,883 B2 | * | 7/2009 | Livengood et al. | 280/87.01 |
| 7,591,786 B2 | * | 9/2009 | Holmberg et al. | 600/437 |
| 7,594,668 B2 | * | 9/2009 | Arceta et al. | 280/47.35 |
| 7,612,999 B2 | * | 11/2009 | Clark et al. | 361/679.4 |
| 7,621,544 B2 | * | 11/2009 | Rossini | 280/79.3 |
| 7,654,261 B1 | * | 2/2010 | Rockhold | 128/204.18 |
| 7,719,420 B2 | * | 5/2010 | Christie et al. | 340/542 |
| 7,791,866 B2 | * | 9/2010 | Clark et al. | 361/679.01 |
| 7,806,376 B2 | * | 10/2010 | Song et al. | 248/177.1 |
| 7,849,859 B2 | * | 12/2010 | Bochner et al. | 128/845 |
| 7,859,836 B2 | * | 12/2010 | Bae | 361/679.55 |
| D643,535 S | * | 8/2011 | Ross et al. | D24/164 |

(Continued)

*Primary Examiner* — John R Olszewski
*Assistant Examiner* — Jacob Meyer

(57) ABSTRACT

A portable nursing service cart preferable includes a top and a bottom platform, a central storage section, front and side access doors, a plurality of sliding drawers and compartments, a top panel for receiving and supporting documents and a pair of apertures formed at opposite lateral ends for assisting a user to grip and transport the body. A plurality of caster wheels is coupled to an underside of the bottom platform. A plurality of display screens are situated on the top platform and spaced above the central storage section. The service cart may house and support a variety of medical equipment and medical records to provide nurses and other health caretakers with a convenient means of simultaneously administering healthcare and administration of patient medical records.

13 Claims, 9 Drawing Sheets

U.S. PATENT DOCUMENTS

| | | | | |
|---|---|---|---|---|
| 7,990,691 B2* | 8/2011 | Clark et al. | | 361/679.01 |
| 8,056,910 B2* | 11/2011 | Deavila | | 280/47.35 |
| 8,075,071 B1* | 12/2011 | Whittall | | 312/249.12 |
| D652,521 S * | 1/2012 | Ross et al. | | D24/185 |
| 8,109,527 B2* | 2/2012 | Bustle et al. | | 280/47.35 |
| 2001/0035702 A1* | 11/2001 | Murphy et al. | | 312/229 |
| 2002/0013640 A1* | 1/2002 | Phoon et al. | | 700/237 |
| 2002/0040954 A1* | 4/2002 | Roberts | | 248/121 |
| 2003/0201697 A1* | 10/2003 | Richardson | | 312/209 |
| 2003/0222548 A1* | 12/2003 | Richardson et al. | | 312/209 |
| 2004/0262867 A1* | 12/2004 | Arceta et al. | | 280/47.35 |
| 2005/0017468 A1* | 1/2005 | Gallant et al. | | 280/47.35 |
| 2006/0125356 A1* | 6/2006 | Meek et al. | | 312/215 |
| 2007/0001413 A1* | 1/2007 | Rossini | | 280/47.35 |
| 2007/0185390 A1* | 8/2007 | Perkins et al. | | 600/300 |
| 2008/0078071 A1* | 4/2008 | Gong | | 24/373 |
| 2008/0251661 A1* | 10/2008 | Rossini | | 248/176.1 |
| 2008/0252045 A1* | 10/2008 | Rossini et al. | | 280/659 |
| 2009/0015116 A1* | 1/2009 | Arceta et al. | | 312/209 |
| 2009/0101219 A1* | 4/2009 | Martini et al. | | 137/565.29 |
| 2009/0212518 A1* | 8/2009 | Bustle et al. | | 280/47.35 |
| 2009/0212670 A1* | 8/2009 | Bustle et al. | | 312/209 |
| 2009/0261549 A1* | 10/2009 | Kral | | 280/47.35 |
| 2009/0319079 A1* | 12/2009 | Arceta et al. | | 700/228 |
| 2010/0148458 A1* | 6/2010 | Ross et al. | | 280/47.34 |
| 2011/0025007 A1* | 2/2011 | Butler et al. | | 280/47.35 |

* cited by examiner

PORTABLE NURSING SERVICE CART AND ASSOCIATED METHOD

CROSS REFERENCE TO RELATED APPLICATIONS

This application claims the benefit of U.S. Provisional Application No. 61/189,254, filed Aug. 15, 2008, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION
TECHNICAL FIELD

This invention relates to medical service carts and, more particularly, to a portable nursing service cart and associated method for providing nurses and other health caretakers with a convenient means of simultaneously administering healthcare and patient medical records.

PRIOR ART

Typically, a nurse is responsible for several patients located at or near a centralized nursing station. At the beginning of a shift, the nursing personnel perform medication rounds during which the appropriate medications are administered to the various patients. A nurse initially loads a medication cart with the medications needed for a medication round. The nurse determines the quantities and types of medications needed by examining the individual orders from the treating physicians for each of her assigned patients. During a round, the nurse must also review the patient's chart, which is typically mounted on the bed of the patient, to ensure the correct administration of medication. Each administration of medication must then be properly recorded and verified on a multitude of charts and forms.

Other medical supplies, such as bandages, gauze, intravenous tubing, needles, etc., may also be dispensed during the nurse's round. Oftentimes, a nurse must retrieve required medical supplies from a centralized supply closet. This procedure is time consuming and tedious. In addition, each of the medical supplies is typically charged to the patient on an "as used" basis and, consequently, an accurate record of the medical supplies expended on a particular patient is required for billing purposes. The nurse thus needs to complete additional forms relating to the use of medical supplies.

All of these procedures are very tedious and time consuming. The attention given to a patient is thus necessarily reduced due to the nurse spending a significant amount of time doing clerical work and retrieving supplies from the supply closet. Human recorders are also prone to inaccurate or incomplete information. These problems are exacerbated when the human recorder has to put forth a great deal of effort in the recording process. In addition, precious time is consumed detecting and resolving errors in the record.

Accordingly, a need remains for a portable nursing service cart in order to overcome the above-noted shortcomings. The present invention satisfies such a need by providing an apparatus which is convenient and easy to use, is durable yet lightweight in design, is versatile in its applications, and provides nurses and other health caretakers with a convenient means of simultaneously administering healthcare and patient medical records.

BRIEF SUMMARY OF THE INVENTION

In view of the foregoing background, it is therefore an object of the present invention to provide a multi-functional portable nursing cart for providing multiple medical treatment functions. These and other objects, features, and advantages of the invention are provided by a portable nursing service cart.

In a preferred embodiment of the present invention, a portable nursing cart may include a body preferably having a top and a bottom platform, and a central storage section intermediately positioned between the top platform and bottom platform. A plurality of display screens may preferably be situated on the top platform and spaced above the central storage section. A plurality of caster wheels may further be coupled to an underside of the bottom platform and spaced from the central storage section. A central processing unit (CPU) may be stored within the central storage section and communicatively coupled to a first one of the display screens.

The central storage section preferably has a pair of front access doors pivotally coupled to an anterior face thereof and further has a side access door pivotally coupled to a lateral face thereof. A blood pressure cuff and monitoring apparatus may be stored within the central storage section and communicatively coupled to a second one of the display screens. Further, a digital thermometer may be stored within the central storage section and communicatively coupled to a third one of the display screens. In addition, the top panel may have a concave shape for receiving and supporting documents thereon and further having a pair of apertures formed at opposite lateral ends thereof for assisting a user to grip and transport the body.

In one embodiment, the central storage section may include a divider wall monolithically formed with top and bottom inner sides of the central storage section such that the central storage section is bifurcated into anterior and posterior regions respectively. A plurality of sliding drawers may be independently situated with the anterior region and remaining isolated from the posterior region. Similarly, a plurality of compartments may be situated within the posterior region and remaining isolated from the anterior region. In addition, the front pair of access doors are located in front of the sliding drawers while the side access door is located at a lateral side of the sliding drawers and the compartments respectively.

In one embodiment, the central storage section further includes a notch formed within a top end thereof, the notch extending from the anterior face of the central storage section and terminating midway to a posterior face of the central storage section. A retractable computer keyboard tray may be slidably interfitted within the notch and may be juxtaposed subjacent to the top platform. A posterior edge of the top platform may be stepped downwardly towards a top surface of the central storage section while the display screens may be located directly on the rear edge of the top platform.

In another embodiment, the bottom platform may include a planar top surface and an outer shoulder monolithically formed with the top surface with the outer shoulder preferably registered orthogonal to an entire circumference of the top surface. The outer shoulder has a top edge and a bottom edge terminating above and below the top surface such that first and second cavities are formed above and below the top surface wherein a bottom end of the central storage section is nested within the first cavity and the caster wheels are located within the second cavity. Each of the compartments may be accessible when the side access door is pivoted to an open position.

The structure of such a portable nursing service cart may advantageously allow a nurse to access a variety of medical equipment and supporting patient records simultaneously and in a most convenient way. The invention may serve as a portable medical station, store and "mini" office all-in-one station thus improving the nurses' efficiency and attention to patients' immediate needs.

The invention may include a method of utilizing a multi-functional portable nursing cart for providing multiple medical treatment functions. The method may include the chronological steps of providing a body preferably having top and bottom platforms and a central storage section intermediately positioned between the top and bottom platforms; providing and spacing a plurality of display screens above the central storage section by situating the display screens on the top platform; providing and spacing a plurality of caster wheels from the central storage section by coupling the caster wheels to an underside of the bottom platform.

Further, the method may include providing and storing a central processing unit (CPU) within the central storage section; communicatively coupling the CPU to a first one of the display screens; providing and pivotally coupling a pair of front access doors to an anterior face of the central storage section; providing and pivotally coupling a side access door to a lateral face of the central storage section; providing and storing a blood pressure cuff and monitoring apparatus within central storage section; communicatively coupling the blood pressure cuff and monitoring apparatus to a second one of the display screens; providing and storing a digital thermometer within the central storage section; and communicatively coupling the digital thermometer to a third one of the display screens.

The method may further provide for the top panel preferably having a concave shape for receiving and supporting documents thereon, the top panel further having a pair of apertures formed at opposite lateral ends thereof for assisting a user to grip and transport the body.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

Figure 1:
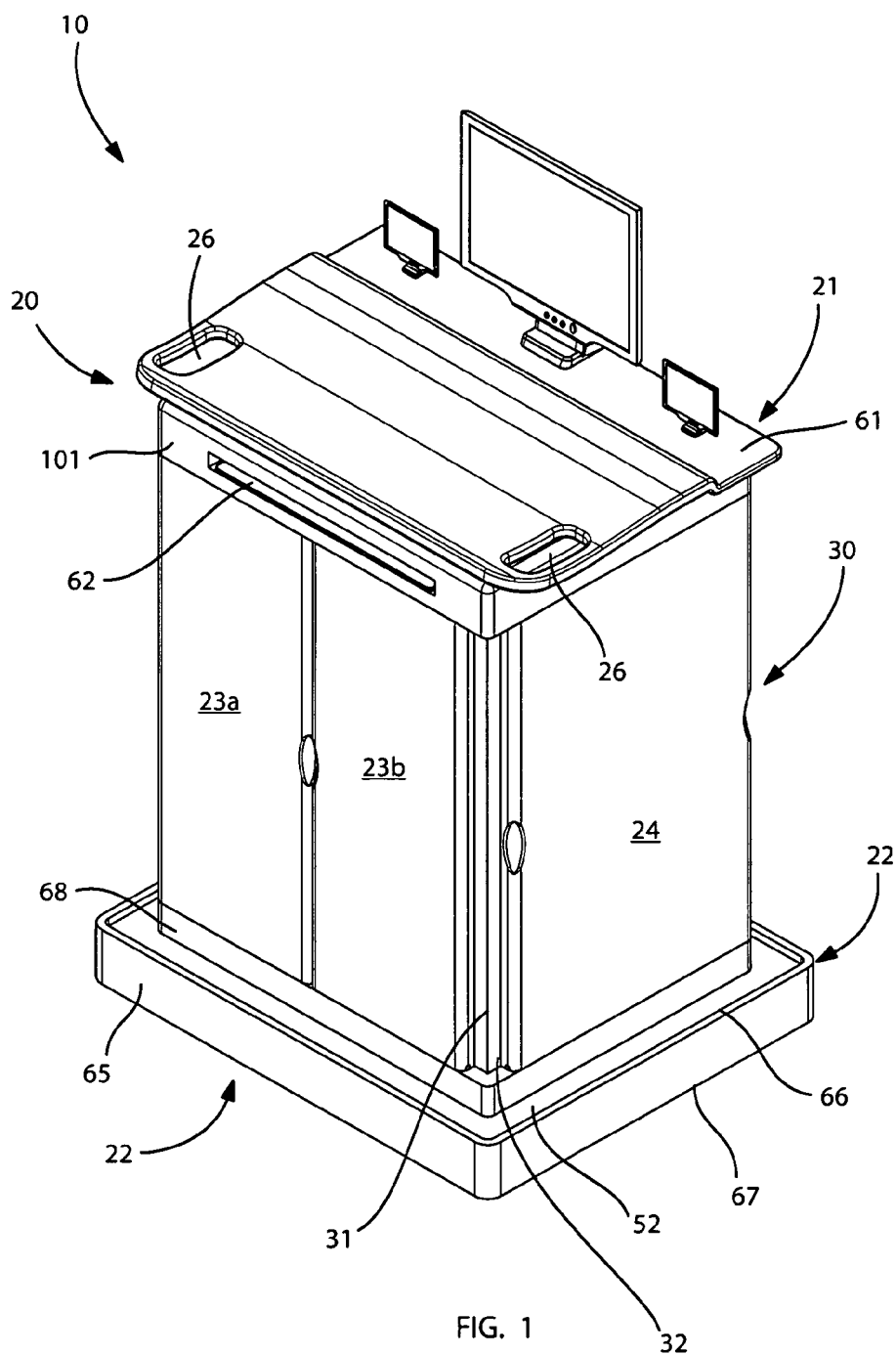
FIG. 1 is a perspective view showing a multi-functional nurse service cart at a closed position, in accordance with the present invention.

Those skilled in the art will appreciate that the figures are not intended to be drawn to any particular scale; nor are the figures intended to illustrate every embodiment of the invention. The invention is not limited to the exemplary embodiments depicted in the figures or the shapes, relative sizes or proportions shown in the figures.

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The apparatus of this invention is referred to generally in FIGS. 1-9 by the reference numeral 10 and is intended to provide a portable nursing service cart. It should be understood that the portable nursing service cart 10 may be used to provide nurses and other health caretakers with a convenient mechanism for administering care to patients while maintaining patient medical records in a succinct and organized manner. Such portable nursing cart 10 may include a body 20 preferably having top and bottom platforms 21, 22, and a central storage section 30 intermediately positioned between the top platform 21 and bottom platform 22. Such a structural configuration provides the unexpected and unpredictable benefit of minimizing operating forces exerting on said central storage section 30, while a caregiver is transporting the cart 10 between remote locations and further while the caregiver is reviewing patient charts and vital signs on the display screens 40.

A plurality of display screens 40 may be situated on the top platform 21 and spaced above the central storage section 30. By using multiple display screens 40, a caregiver is able to quickly view and identify abnormal vital signs without having to toggle one screen between multiple views. A plurality of caster wheels 80 may be coupled to an underside of the bottom platform 22 and thereby spaced from the central storage section 30. A central processing unit (CPU) 41 may be stored within the central storage section 30 and communicatively coupled to a first one 40a of the display screens 40.

Referring to FIGS. 1, 2, 4 and 8, the central storage section 30 preferably has a pair of front access doors 23a, 23b pivotally coupled to an anterior face 31 of the central storage section 30. A side access door 24 is pivotally coupled to a lateral face 32 of the central storage section 30. A blood pressure cuff and monitoring apparatus 90 may be stored within the central storage section 30 and communicatively coupled to a second one 40b of the display screens 40. Further, a digital thermometer 91 may be stored within the central storage section 30 and communicatively coupled to a third one 40c of the display screens 40. The storage of the blood pressure cuff and monitoring apparatus 90 in combination with the digital thermometer 91, overcomes the shortcoming of requiring the nurse to manually carry such items between patient rooms, which is cumbersome and dangerous during long work shifts at the hospital.

Referring to FIGS. 5-8, the top platform 21 may preferably have a concave shape for receiving and supporting documents thereon. Such a top platform 21 further has a pair of apertures 26 formed at opposite lateral ends thereof for assisting a user to grip and transport the body 20. By forming the apertures 26 at the top platform, the caregiver can pull and push the entire cart 10 without directly engaging the central storage section 30. Further, apertures 26 permit the use to remove the top platform 21 from the central storage section 30 by detaching a plurality of quick-connect coupling (not shown) mated to a top surface of the central storage section 30.

Figure 2:
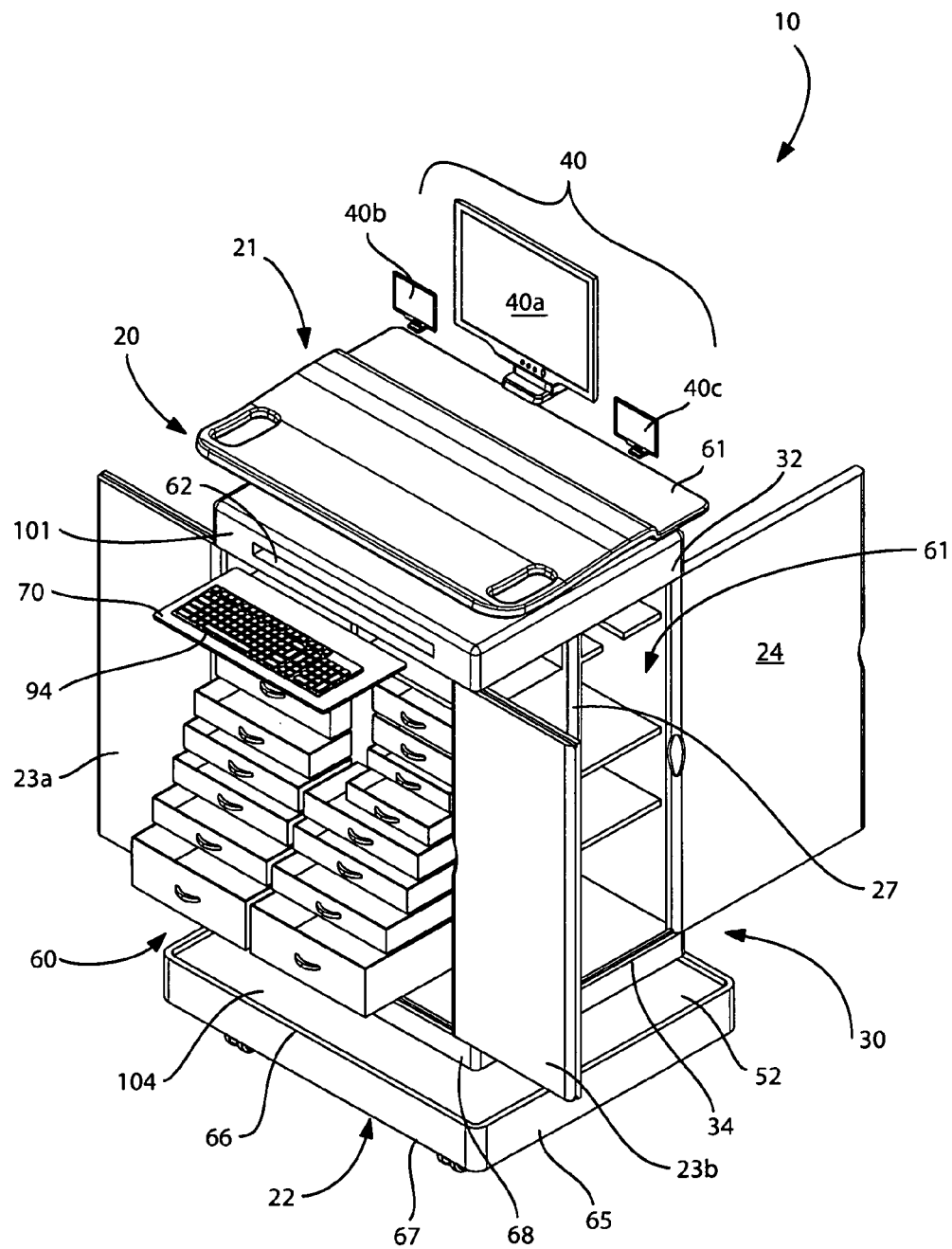
FIG. 2 is a perspective view showing the cart of FIG. 1 at an open position.
Figure 3:
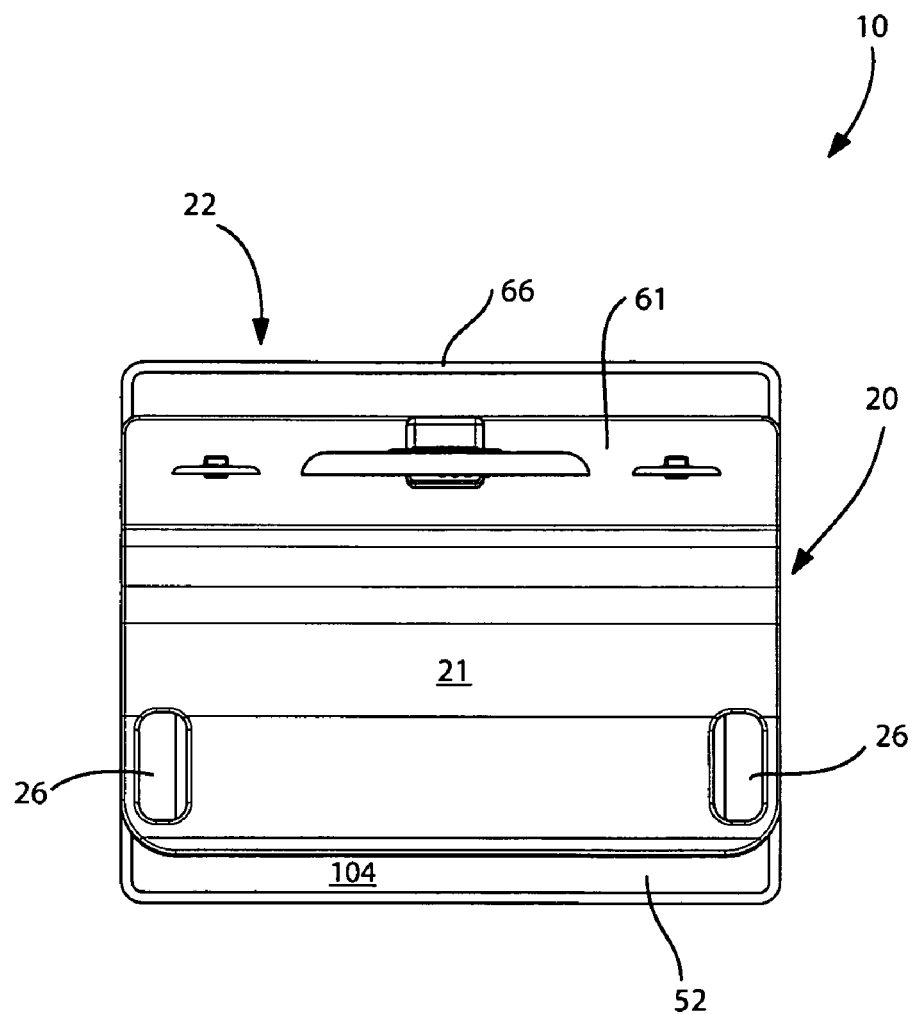
FIG. 3 is a top plan view of the cart shown in FIG. 1.
Figure 4:
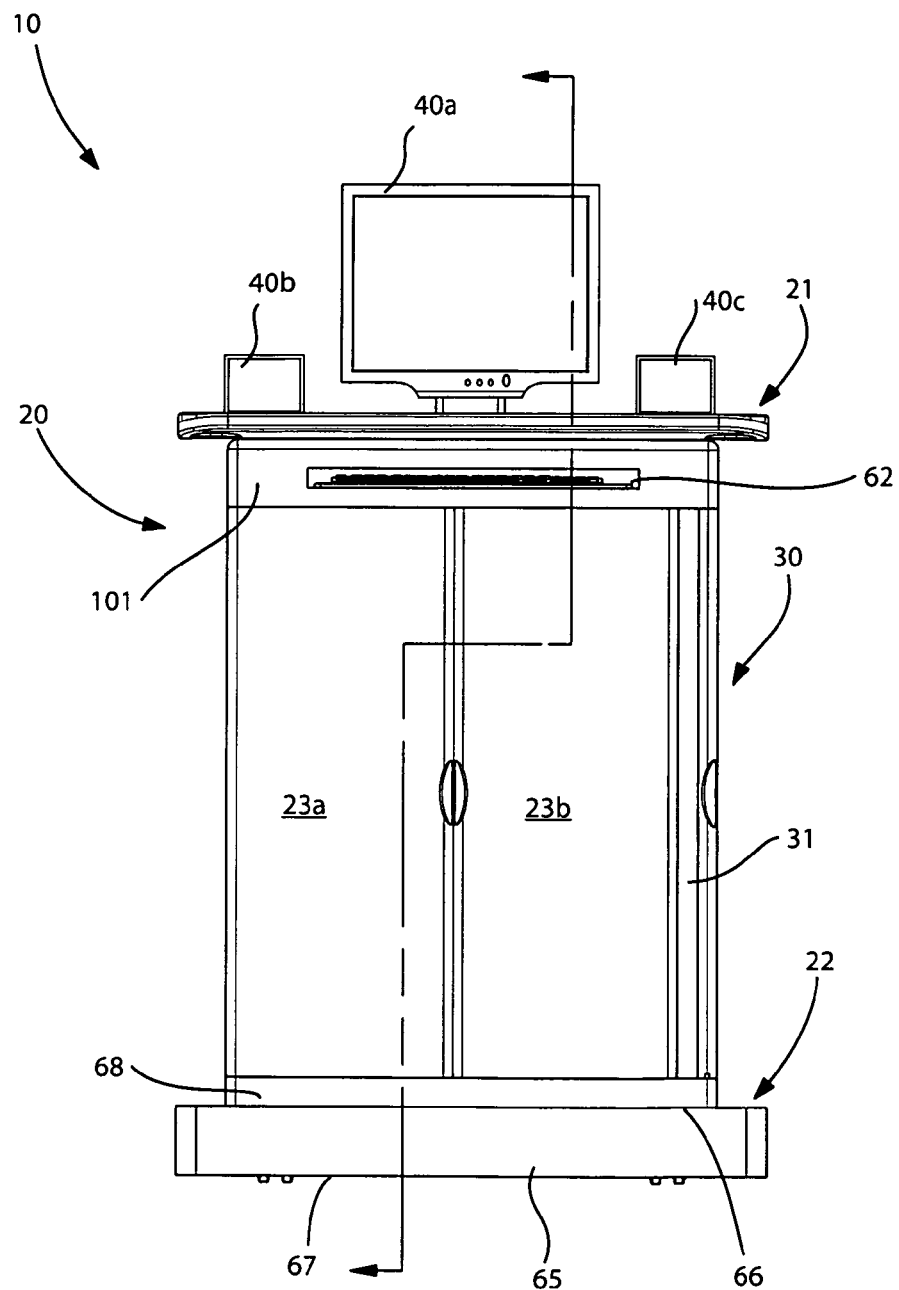
FIG. 4 is a front elevational view of the cart shown in FIG. 1.
Figure 5:
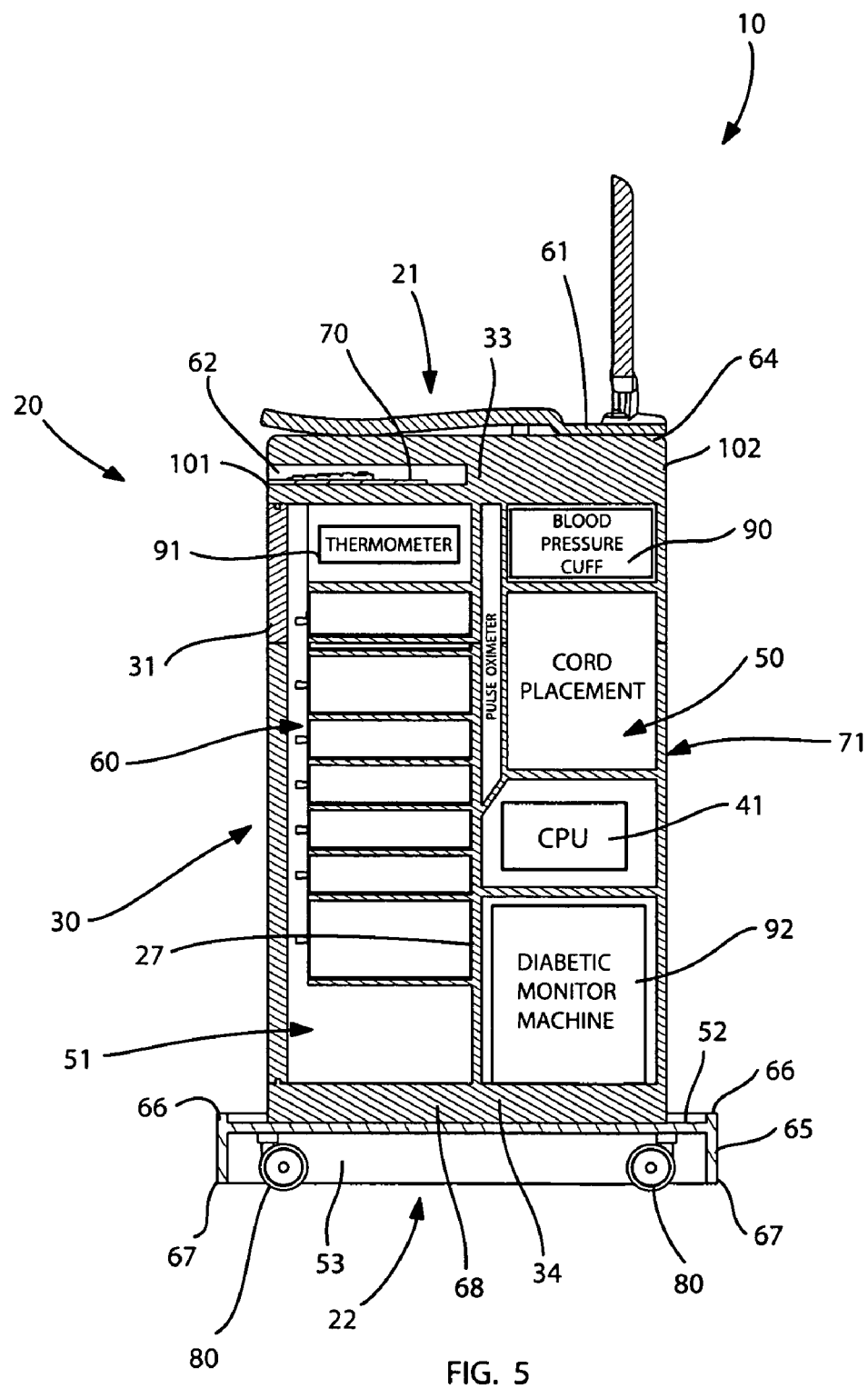
FIG. 5 is a cross-sectional view taken along line 5-5 in FIG. 4 wherein the anterior and posterior regions are defined by the divider wall.
Figure 6:
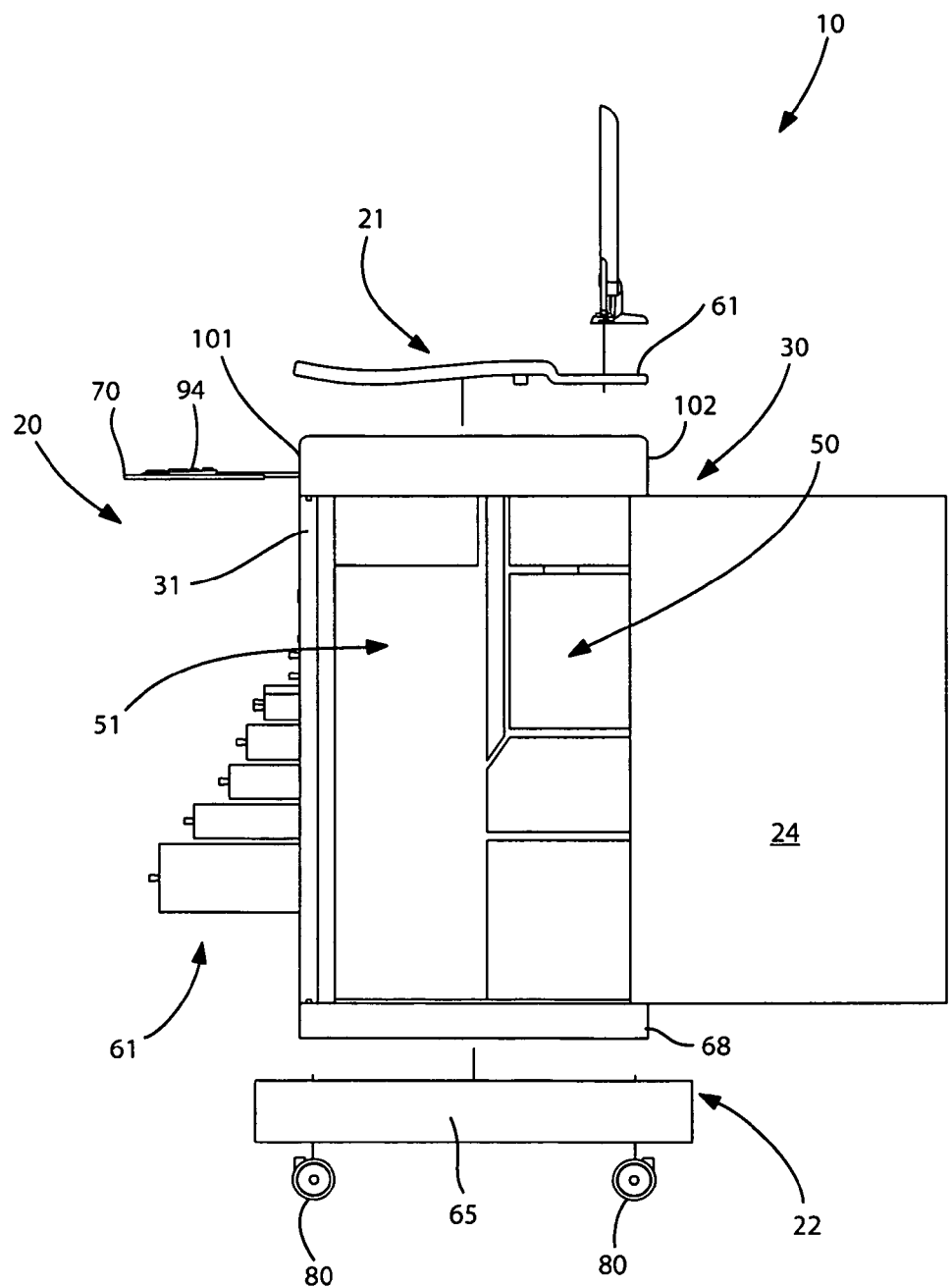
FIG. 6 is a side elevational view of the cart shown in FIG. 2.
Figure 7:
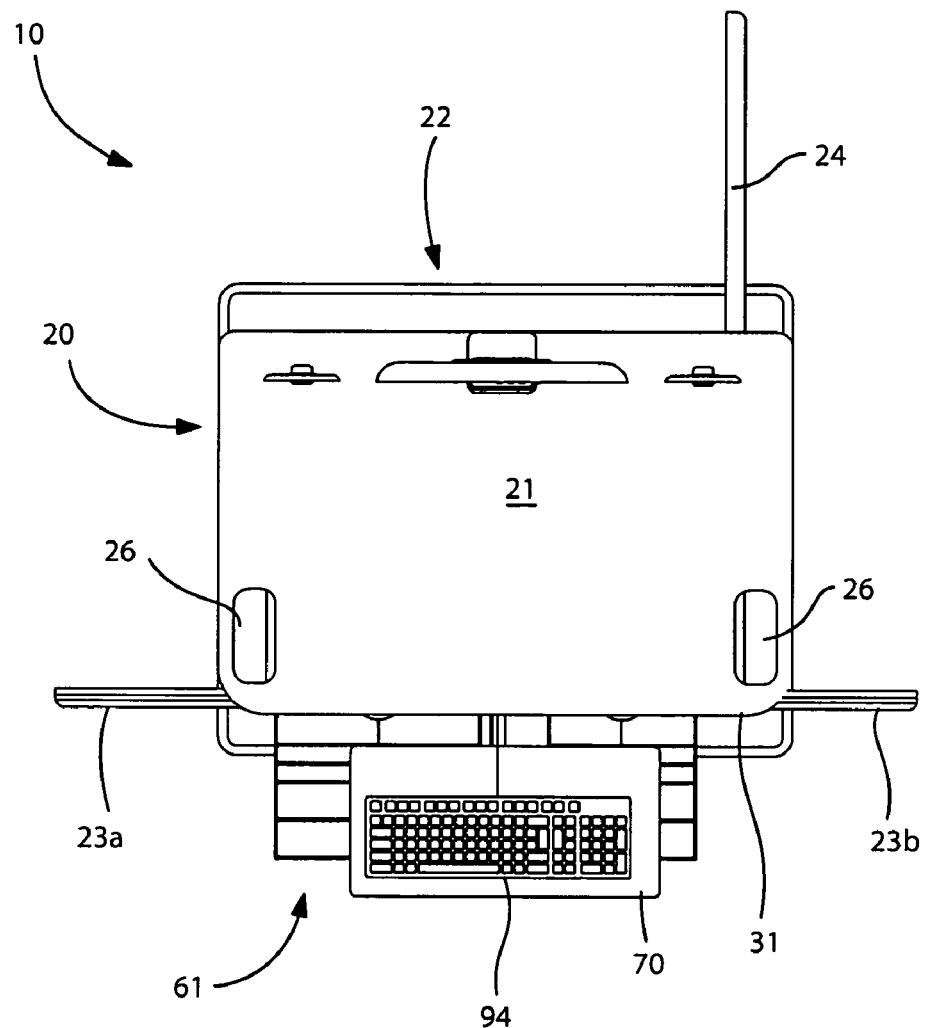
FIG. 7 is a top plan view of the cart shown in FIG. 2.
Figure 8:
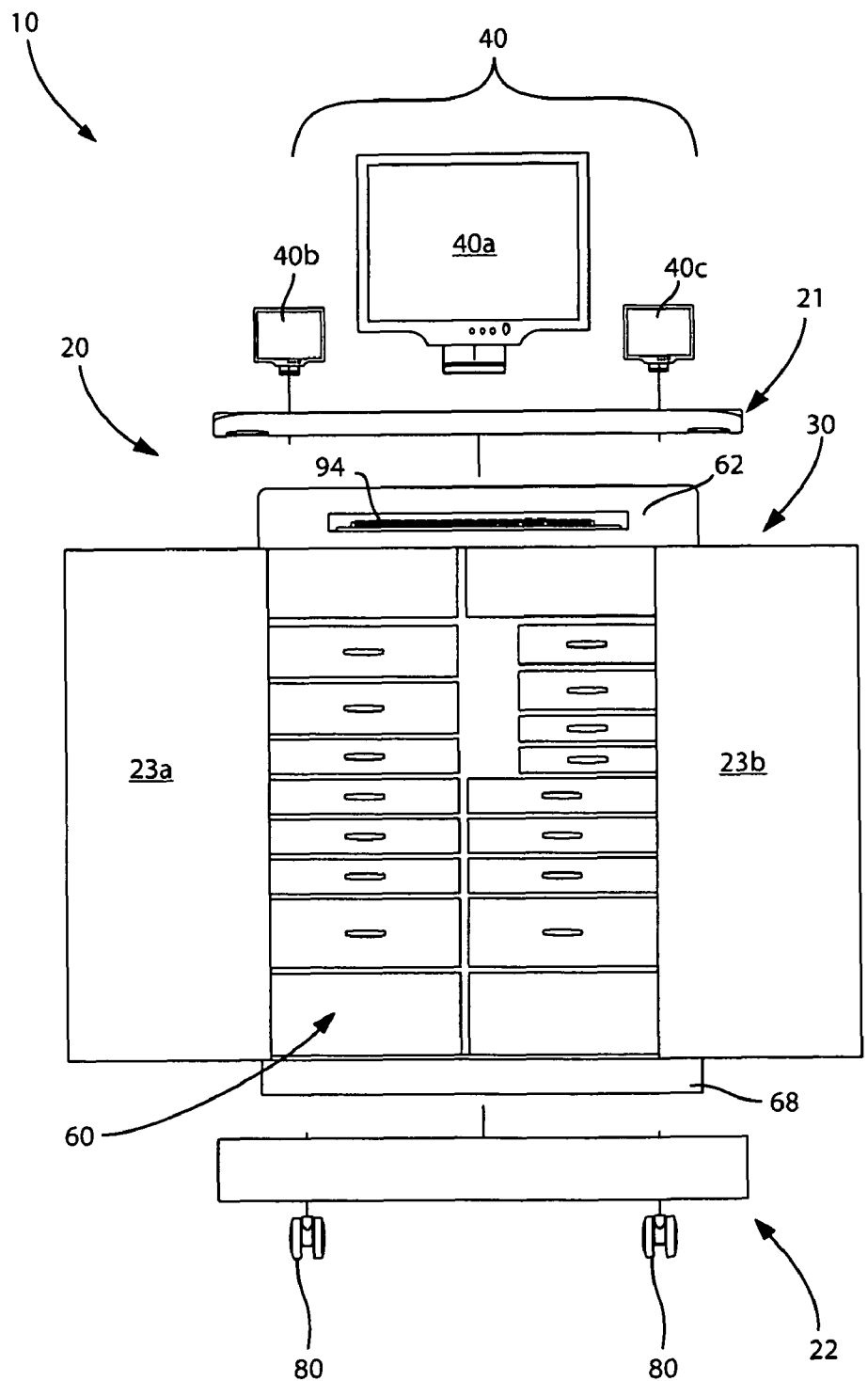
FIG. 8 is an exploded view showing the separation between the central storage section and the top and bottom platforms.
Figure 9:
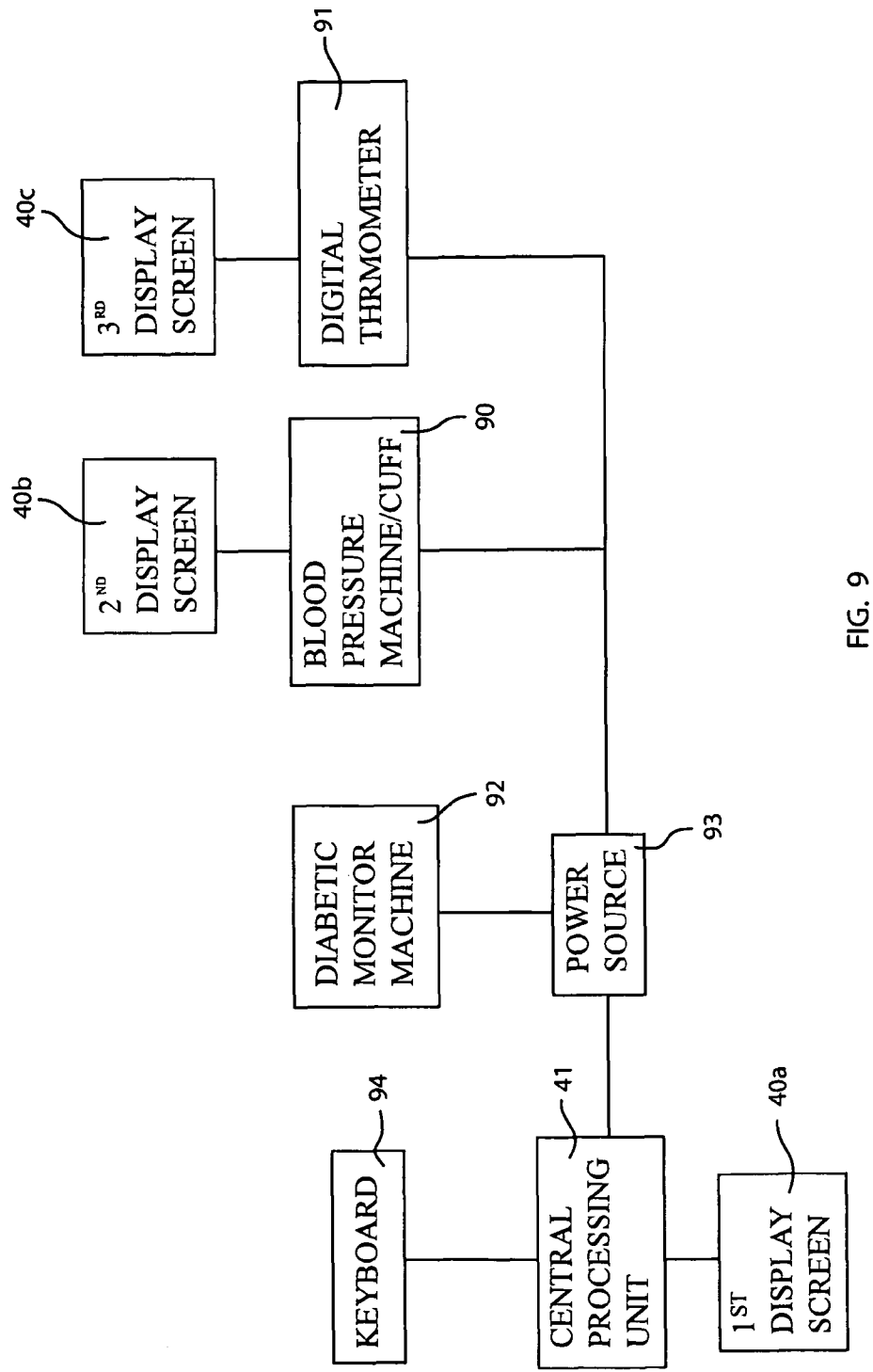
FIG. 9 is a high-level schematic block diagram showing the interrelationship between the major electrical components of present invention.

Referring to FIGS. 2, 5 and 8, the central storage section 30 may include a divider wall 27 monolithically formed with top 33 and bottom inner sides 34 of the central storage section 30 such that the central storage section 30 is bifurcated into anterior 51 and posterior 50 regions, respectively. A plurality of sliding drawers 60 may be independently situated with the anterior region 51 and thereby remain isolated from the posterior region 50. Similarly, a plurality of compartments 61 may be situated within the posterior region 50 and thereby remain isolated from the anterior region 51. In addition, each front access door 23a, 23b is located in front of the sliding drawers 60 while the side access door 24 is located at a lateral side of the sliding drawers 60 and the compartments 61 respectively. Such a structural configuration provides the unpredicted and unexpected benefit of permitting the caregiver to quickly and easily access the anterior region 51 via either the front doors 23a, 23b or side door 24. Each of the compartments 61 is accessible when the side access door 24 is pivoted to an open position. The posterior region 50 is accessible only by opening the side access door 24, so that unauthorized personnel are prohibited from removing the electronic patient analysis devices 90, 92. For example, a registered nurse RN may have access to the posterior region 50 while a nurse's aid has access to only the anterior region 51.

Referring to FIGS. 1, 2, 4, 5 and 8, the central storage section 30 further includes a notch 62 formed within a top end 63 thereof, such as the top inner side 33. Such a notch 62 preferably extends from the anterior face 101 of the central storage section 30 and terminates midway to the posterior face 102 of the central storage section 30. A retractable computer keyboard tray 70 may be slidably interfitted within the notch 62 and may be juxtaposed subjacent to the top platform 21. In this manner, a keyboard 94 may be hidden within the notch 62 during non-operating conditions.

Notably, a posterior edge 61 of the top platform 21 is stepped downwardly towards a top surface 64 of the central storage section 30 wherein the display screens 40 may be located directly on the posterior edge 71 of the top platform 21. Such a structural configuration provides the unexpected and unpredictable advantage of weighing down the top platform 21 while patient charts and documents are displayed on the concave surface of the top platform 21. In this manner, a caregiver is able to quickly shuffle documents around on the top platform 21, while minimizes a risk of accidentally displacing the display screens 40 from the cart 10.

Referring to FIGS. 1, 2, 4, 5, 6, and 8, the bottom platform 22 may include a planar top surface 64 and an outer shoulder 65 monolithically formed with the top surface 64. Such an outer shoulder 65 is preferably registered orthogonal to an entire circumference of the top surface 104. The outer shoulder 65 has a top edge 66 and a bottom edge 67 terminating above and below the top surface 104 such that first and second cavities 52, 53 are formed above and below the top surface 104, respectively. In this manner, a bottom end 68 of the central storage section 30 is advantageously nested within the first cavity 52 and the caster wheels 50 are advantageously located within the second cavity 53. Such a structural configuration provides the unexpected and unpredictable benefit of prohibiting a caregiver's foot from being run over by the casters and also provides a buffer region along which said central storage section 30 may laterally slide during space-limited areas often found in hospitals.

The present invention may include a method of utilizing a multi-functional portable nursing cart 10 for providing multiple medical treatment functions. The method may include the chronological steps of: providing a body 20 preferably having top and bottom platforms 21, 22 and a central storage section 30 intermediately positioned between the top and bottom platforms 21, 22; providing and spacing a plurality of display screens 40 above the central storage section 30 by situating the display screens 40 on the top platform 21; providing and spacing a plurality of caster wheels 50 from the central storage section 30 by coupling the caster wheels 50 to an underside of the bottom platform 22.

Further, the method may include the chronological steps of: providing and storing a central processing unit (CPU) 41 within the central storage section 30; communicatively coupling the CPU 41 to a first one 40a of the display screens 40; providing and pivotally coupling a pair of front access doors 23 to an anterior face 31 of the central storage section 30; providing and pivotally coupling a side access door 24 to a lateral face 32 of the central storage section 30; providing and storing a blood pressure cuff and monitoring apparatus 90 within the central storage section 30; communicatively coupling the blood pressure cuff and monitoring apparatus 90 to a second one 40b of the display screens 40; providing and storing a digital thermometer 91 within the central storage section 30; and communicatively coupling the digital thermometer 91 to a third one 40c of the display screens 40.

The top panel 25 may have a concave shape for receiving and supporting documents thereon. Such a top panel 25 may further have a pair of apertures 26 formed at opposite lateral ends thereof for assisting a user to grip and transport the body 20.

The present invention, as claimed, provides the unexpected and unpredictable benefit of consolidating a nurse's most frequently used equipment in combination with a CPU communicatively coupled to a display screen for providing access to the patients' medical records. Through use of the present invention, nurses can conveniently find everything they are likely to need, right at their fingertips. By using the device, nurses' productivity are tremendously enhanced, and their number and frequency of extra trips to the nurses' station may be drastically reduced. The combination of such claimed elements provides an unpredictable and unexpected result which is not rendered obvious by one skilled in the art.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A multi-functional portable nursing cart for providing multiple medical treatment functions, said portable nursing cart comprising:
   a body having top and bottom platforms and a central storage section positioned between said top and bottom platforms;
   a plurality of display screens situated on said top platform and spaced above said central storage section;
   a plurality of caster wheels coupled to an underside of said bottom platform and spaced from said central storage section;
   a central processing unit (CPU) stored within said central storage section and communicatively coupled to a first one of said display screens, said central storage section having a pair of front access doors pivotally coupled to an anterior face thereof, said central storage section further having a side access door pivotally coupled to a lateral face thereof;
   a blood pressure cuff and monitoring apparatus stored within said central storage section and communicatively coupled to a second one of said display screens; and
   a digital thermometer stored within said central storage section and communicatively coupled to a third one of said display screens;
   wherein said top platform has a concave shape for receiving and supporting documents thereon.

2. The multi-functional portable nursing cart of claim 1, wherein said central storage section comprises:
   a divider wall monolithically formed with top and bottom inner sides of said central storage section such that said central storage section is bifurcated into anterior and posterior regions respectively;
   a plurality of sliding drawers independently situated with said anterior region and remaining isolated from said posterior region; and
   a plurality of compartments situated within said posterior region and remaining isolated from said anterior region;
   wherein said front pair of access doors are located in front of said sliding drawers;
   wherein said side access door is located at a lateral side of said sliding drawers and said compartments respectively.

3. The multi-functional portable nursing cart of claim 2, wherein said central storage section further includes:
   a notch formed within a top end thereof, said notch extending from said anterior face of said central storage section and terminating midway to a posterior face of said central storage section; and
   a retractable computer keyboard tray slidably interfitted within said notch and being juxtaposed subjacent to said top platform.

4. The multi-functional portable nursing cart of claim 3, wherein a posterior edge of said top platform is stepped downwardly towards a top surface of said central storage section, said display screens being located directly on said posterior edge of said top platform.

5. The multi-functional portable nursing cart of claim 3, wherein said bottom platform comprises:
   a planar top surface; and
   an outer shoulder monolithically formed with said top surface, said outer shoulder being registered orthogonal to an entire circumference of said top surface;
   wherein said outer shoulder has a top edge and a bottom edge terminating above and below said top surface such that first and second cavities are formed above and below said top surface;
   wherein a bottom end of said central storage section is nested within said first cavity and said caster wheels are located within said second cavity.

6. The multi-functional portable nursing cart of claim 2, wherein each of said compartments is accessible when said side access door is pivoted to an open position.

7. A multi-functional portable nursing cart for providing multiple medical treatment functions, said portable nursing cart comprising:
   a body having top and bottom platforms and a central storage section intermediately positioned between said top and bottom platforms;
   a plurality of display screens situated on said top platform and spaced above said central storage section;
   a plurality of caster wheels coupled to an underside of said bottom platform and spaced from said central storage section;
   a central processing unit (CPU) stored within said central storage section and communicatively coupled to a first one of said display screens, said central storage section having a pair of front access doors pivotally coupled to an anterior face thereof, said central storage section further having a side access door pivotally coupled to a lateral face thereof;
   a blood pressure cuff and monitoring apparatus stored within said central storage section and communicatively coupled to a second one of said display screens; and
   a digital thermometer stored within said central storage section and communicatively coupled to a third one of said display screens;
   wherein said top platform has a concave shape for receiving and supporting documents thereon, said top platform further having a pair of apertures formed at opposite lateral ends thereof for assisting a user to grip and transport said body.

8. The multi-functional portable nursing cart of claim 7, wherein said central storage section comprises:
   a divider wall monolithically formed with top and bottom inner sides of said central storage section such that said central storage section is bifurcated into anterior and posterior regions respectively;
   a plurality of sliding drawers independently situated with said anterior region and remaining isolated from said posterior region; and
   a plurality of compartments situated within said posterior region and remaining isolated from said anterior region;
   wherein said front pair of access doors are located in front of said sliding drawers;

wherein said side access door is located at a lateral side of said sliding drawers and said compartments respectively.

9. The multi-functional portable nursing cart of claim 8, wherein said central storage section further includes:
   a notch formed within a top end thereof, said notch extending from said anterior face of said central storage section and terminating midway to a posterior face of said central storage section; and
   a retractable computer keyboard tray slidably interfitted within said notch and being juxtaposed subjacent to said top platform.

10. The multi-functional portable nursing cart of claim 9, wherein a posterior edge of said top platform is stepped downwardly towards a top surface of said central storage section, said display screens being located directly on said posterior edge of said top platform.

11. The multi-functional portable nursing cart of claim 9, wherein said bottom platform comprises:
   a planar top surface; and
   an outer shoulder monolithically formed with said top surface, said outer shoulder being registered orthogonal to an entire circumference of said top surface;
   wherein said outer shoulder has a top edge and a bottom edge terminating above and below said top surface such that first and second cavities are formed above and below said top surface;
   wherein a bottom end of said central storage section is nested within said first cavity and said caster wheels are located within said second cavity.

12. The multi-functional portable nursing cart of claim 8, wherein each of said compartments is accessible when said side access door is pivoted to an open position.

13. A method of utilizing a multi-functional portable nursing cart for providing multiple medical treatment functions, said method comprising the chronological steps of:
   providing a body having top and bottom platforms and a central storage section intermediately positioned between said top and bottom platforms;
   providing and spacing a plurality of display screens above said central storage section by situating said display screens on said top platform;
   providing and spacing a plurality of caster wheels from said central storage section by coupling said caster wheels to an underside of said bottom platform;
   providing and storing a central processing unit (CPU) within said central storage section;
   communicatively coupling said CPU to a first one of said display screens;
   providing and pivotally coupling a pair of front access doors to an anterior face of said central storage section;
   providing and pivotally coupling a side access door to a lateral face of said central storage section;
   providing and storing a blood pressure cuff and monitoring apparatus within said central storage section;
   communicatively coupling said blood pressure cuff and monitoring apparatus to a second one of said display screens;
   providing and storing a digital thermometer within said central storage section; and
   communicatively coupling said digital thermometer to a third one of said display screens;
   wherein said top platform has a concave shape for receiving and supporting documents thereon, said top platform further having a pair of apertures formed at opposite lateral ends thereof for assisting a user to grip and transport said body.

\* \* \* \* \*